US008302597B2

United States Patent
Beely et al.

(10) Patent No.: US 8,302,597 B2
(45) Date of Patent: Nov. 6, 2012

(54) MEDICAL TUBE SECURING DEVICE

(75) Inventors: Brendan M. Beely, San Antonio, TX (US); Gabriel R. Wright, Converse, TX (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 367 days.

(21) Appl. No.: 12/573,371

(22) Filed: Oct. 5, 2009

(65) Prior Publication Data

US 2010/0083970 A1    Apr. 8, 2010

Related U.S. Application Data

(60) Provisional application No. 61/102,910, filed on Oct. 6, 2008.

(51) Int. Cl.
*A61M 16/00* (2006.01)
*A61C 5/00* (2006.01)
*A61B 1/267* (2006.01)

(52) U.S. Cl. ......... 128/200.26; 128/202.27; 128/204.18; 128/207.14; 128/207.17; 128/DIG. 26; 600/195; 433/18; 433/19; 433/195

(58) Field of Classification Search ................... 128/859, 128/861, 200.26, 202.27, 204.18, 207.14, 128/207.17; 600/195; 433/18, 19, 195
See application file for complete search history.

(56) References Cited

U.S. PATENT DOCUMENTS

| | | | | |
|---|---|---|---|---|
| 1,450,419 | A | * | 4/1923 | Heidbrink ...................... 600/237 |
| 2,669,988 | A | | 2/1954 | Carpenter |
| 2,694,397 | A | * | 11/1954 | Herms .......................... 128/861 |
| 2,708,931 | A | * | 5/1955 | Freedland ...................... 128/861 |
| 4,167,814 | A | * | 9/1979 | Schubert .......................... 433/93 |
| 4,233,775 | A | * | 11/1980 | Neufeld .......................... 446/370 |
| 4,270,531 | A | | 6/1981 | Blachly et al. |
| 4,425,911 | A | | 1/1984 | Luomanen et al. |
| 4,832,019 | A | | 5/1989 | Weinstein et al. |
| 4,867,154 | A | * | 9/1989 | Potter et al. .............. 128/207.17 |
| 5,345,931 | A | | 9/1994 | Battaglia, Jr. |
| 5,386,821 | A | | 2/1995 | Poterack |
| 5,419,319 | A | | 5/1995 | Werner |
| 5,490,504 | A | * | 2/1996 | Vrona et al. ............. 128/207.17 |
| 5,626,128 | A | | 5/1997 | Bradley et al. |
| 5,655,519 | A | * | 8/1997 | Alfery ...................... 128/200.26 |
| 5,730,599 | A | * | 3/1998 | Pak .............................. 433/215 |
| 5,806,516 | A | | 9/1998 | Beattie |
| 5,868,132 | A | * | 2/1999 | Winthrop et al. ......... 128/207.14 |
| 5,927,276 | A | * | 7/1999 | Rodriguez ............... 128/207.17 |
| 5,941,246 | A | | 8/1999 | Roopchand |
| 6,067,985 | A | | 5/2000 | Islava |
| 6,098,627 | A | * | 8/2000 | Kellner et al. ................. 128/859 |

(Continued)

OTHER PUBLICATIONS

Smooth-On, Shore Hardness Scales, Copyright 2008, whole document.*

(Continued)

*Primary Examiner* — Clinton T Ostrup

(74) *Attorney, Agent, or Firm* — Elizabeth Arwine

(57) ABSTRACT

A medical tube securing device for a patient is disclosed, comprising at least one bite block and a support frame integral with said bite block, said support frame comprising a protruding extension with at least one inwardly recessed portion so as to avoid contact with the patient's mouth, said protruding extension operable to receive an adjustable medical tube retaining device without contacting the face of the patient.

6 Claims, 5 Drawing Sheets

U.S. PATENT DOCUMENTS

| | | | | |
|---|---|---|---|---|
| 6,241,521 B1 | * | 6/2001 | Garrison | 433/140 |
| 6,436,034 B1 | * | 8/2002 | Funatogawa | 600/238 |
| 6,890,322 B2 | | 5/2005 | Bertoch et al. | |
| 2005/0103331 A1 | | 5/2005 | Wedemeyer | |
| 2005/0252514 A1 | | 11/2005 | Taljaard | |
| 2008/0230055 A1 | * | 9/2008 | NaPier | 128/200.26 |

OTHER PUBLICATIONS

Anchor Fast, Oral Endotracheal Tube Fastener Marketing Brochure, 2007 Hollister Inc., 909927-907.

* cited by examiner

MEDICAL TUBE SECURING DEVICE

REFERENCE TO RELATED APPLICATIONS

This application claims the benefit of U.S. Provisional Application No. 61/102,910 filed Oct. 6, 2008, the entirety of which is specifically and entirely incorporated by reference herein.

RIGHTS IN THE INVENTION

This invention was made with support from the United States Government and, specifically, the United States Army Institute of Surgical Research and, accordingly, the United States government has certain rights in this invention.

FIELD AND BACKGROUND OF THE INVENTION

The invention relates generally to a novel device for securing medical tubes and catheters intubated within a patient.

Endotracheal intubation, placement of a tube into the trachea, is an integral part of airway management in modern-day medical practice where among the variety of concerns are guaranteeing a patient airway, delivery of oxygen to the lungs, and allowing for the removal of expectorant. Intubation plays a vital role in unconscious patients, patients under or emerging from general anesthesia, victims require acute resuscitation, and various patients need chronic or critical intensive medical care.

In various medical procedures, it is common to introduce a catheter into a patient's airway through the mouth. One type of catheter is an endotracheal tube, which is adapted to be inserted through the oral cavity of a patient and into the trachea, for example, to provide for the supply of fluids to the body, for the monitoring of internal conditions in the body and for removal of secretions from within the body. Other examples of catheters include respiratory tubes for laryngeal masks, oral gastric tubes, and esophageal stethoscopes.

After intubation, patient's airway is reasonably secured but not guaranteed. Failure to fasten an endotracheal tube properly may cause dislodgment or displacement of the tube, or even accidental extubation. These complications usually are life-threatening or even fatal.

Another problem is that the catheter is usually relatively easy to deform as it passes between the patient's teeth when inserted orally, it is desirable to prevent the lumen of the catheter from being occluded by a patient's teeth when the patient attempts to bite down. Occlusion of the catheter can lead to, for example, hypoxia, hypercarbia, and the syndrome known as negative pressure pulmonary edema. The endotracheal tube may be kinked, dislodged, or accidently extubated or being bitten by the patient, particularly when the patient is semiconscious and not paralyzed. The situations are usually fatal particularly when a wire reinforced endotracheal tube is used.

A number of approaches have been proposed to address the problems presented above. Bite blocks can be effective in keeping a patient's jaw open and thus prevent the teeth from clamping down on the catheter. One problem with a bite block is that it may get loose within the oral cavity and move from its position down into the patient's throat or airway. If this occurs, then the airway may become partially or completely blocked. Another problem inherent with the use of bite blocks is that they typically concentrate the force exerted by the patient's mandibular contraction on one or two incisors resulting in documented instances of dental disruption and loss.

Presently, adhesives are used to keep the tube positioned which are ineffective because of the presence of facial hair, oily skin, dirt, blood, etc. According to this approach of retaining a medical tube near the tube insertion site, one or more adhesive strips are applied directly over the tube and to the skin of the patient. In order to adjust the position of the tube, the adhesive strip must be removed from the skin and then reapplied in the desired location. This significantly weakens the holding strength of the adhesive, and often requires the placement of additional strips on the tube and skin to properly anchor the tube. Natural body secretions further reduce the ability of the strip to properly retain the tube.

Alternatives to adhesives are known in the art, including the use of straps and harnesses used to secure the medical device around the patient's oral cavity. A common problem with this technique, however, is that the strap rubs against the cheeks and the sensitive tissue at the corners of the mouth, resulting in angular cheilitis (also called perlèche, cheilosis or angular stomatitis) and infection. This is even more of a problem when a patient presents with burns on the face, head and neck which preclude the use of adhesives or irritating straps due to the delicate condition of the affected skin.

U.S. Pat. No. 5,655,519 to Alfrey discloses a patient airway bite block that may be used together with laryngeal mask airways, oral endotracheal tubes and similar patient airways (col. 1, lines 4-7). The bite block comprises a handle for positioning the bite block within the patient's mouth and for removing the bite block therefrom (col. 3, lines 53-58; col. 8. Lines 25-43; FIGS. 1, 5 and 7). The Alfrey device does not address the problem of preventing damage to the skin of the patient, particularly the corners of the mouth. Indeed, the handle of Alfrey is in direct contact with the corners of the patient mouth and would stay in direct contact, causing irritation and subsequent tissue damage, for as long as the Alfrey device is being used on the patient for airway control (FIGS. 7 and 8).

U.S. Pat. No. 5,490,504 to Vrona et al., sold on the market as the ANCHOR FAST™ Oral Endotracheal Tube Fastener by Hollister, Inc., Libertyville, Ill. discloses an endotracheal tube attachment device for positively securing an endotracheal tube to a patient and allowing selective lateral positioning of the tube without removing the same from the patient by means of a tracked device (Abstract; FIG. 5). The Vrona device does not address the problem of keeping a patient's jaw open to prevent the teeth from clamping down on the catheter, or the commensurate problem of dental disruption and loss due to long term mandibular contraction. Furthermore, the Vrona device does not address the problem of preventing damage to the skin of the patient, particularly the upper lip and cheeks (col. 4, lines 10-18; FIG. 5), making the device unsuitable for use with burn victims and patients with sensitive skin.

Therefore, there exists a need for a medical tube securing device that addresses the problems inherent with current bite blocks, straps and harnesses.

SUMMARY OF THE INVENTION

A medical tube securing device for a patient is disclosed, comprising at least one bite block and a support frame integral with said bite block, said support frame comprising a protruding extension with at least one inwardly recessed portion.

The invention is a device to manage endotracheal or gastric tubes as they are used during patient care. The device incorporates semi-rigid bite blocks to prevent tooth damage and a heavy wire framework to manage the tubes. This device is designed to utilize the molars, which provide a greater surface area to distribute the force between two smaller blocks, one placed on each side of the mouth. Protruding from one block to the other is a length of strong yet flexible wire, fashioned so as to contain two loops, as well as a semi-circular portion which protrudes from the patient's mouth. Along this semi-circular portion, a saw toothed track is attached. Able to traverse this track will be a clamping device for securing both endotracheal and gastric tubes. The wire is fashioned in such a manner as to avoid contact with the corners of the patient's mouth. The loops in said wire, which serve as attachment points for the securing straps, are placed in such a way as to move the securing straps completely away from the corners of the mouth. This configuration also prevents the possible migration of the bite blocks into the patient's airway.

The invention addresses several shortcomings associated with the current state of the art for bite blocks and endotracheal/gastric tubes. The device moves the bite blocks (one for each side) from the front teeth to the molars, to capitalize on the greater strength of these teeth to prevent tooth damage, as can occur to incisors with the current bite block. In addition, positioning the bite blocks at the molars prevents the incisor teeth from biting and occluding the endotracheal or nasogastric tubes. The bite blocks are attached to and positioned on a heavy wire framework, which protrudes from the patient's mouth, and which provides attachment sites for straps to secure the device to the patient, and a track and clamp system to secure the endotracheal or nasogastric tubes. The attachment sites are an improvement in capability over the current state of the art, in which the tubes are taped to the bite block and the combined structure is then taped to the patient. The current method can damage the corners of the patient's mouth. The attachment for the breathing tube consists of a saw-toothed track upon which rests a movable attachment strap. The rationale for the track is that it allows the tube to be moved from one side of the mouth to the other to aid in oral care, as well as enable to the tube to be moved should it be irritating a portion of the interior of the mouth. The elongate wire frame contains loops for securing the device to the patient's head in a way that avoids contacting the patient's face. The attachment for the breathing tube consists of a saw-toothed track upon which rests a movable attachment strap.

It is an object of the present invention to prevent dental disruption of an intubated patient through the use of a pair of bite blocks that are limited to only the molars.

It is another object of the present invention to avoid damage to the mouth and face of the intubated patient through the use of an elongate frame that curves or tapers inwardly at the corners of the mouth to avoid tearing the corners of the mouth; and the location of the securing strap, which avoids contact with the corners of the mouth.

A further object of the present invention is to provide a means of securing medical tubes being used on burn patients whose unique medical condition makes the use of conventional securing devices and adhesives impractical or impossible.

It is yet another object of the present invention to allow for proper oral care of the intubated patient while maintaining endotracheal tube security.

The various features of novelty that characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
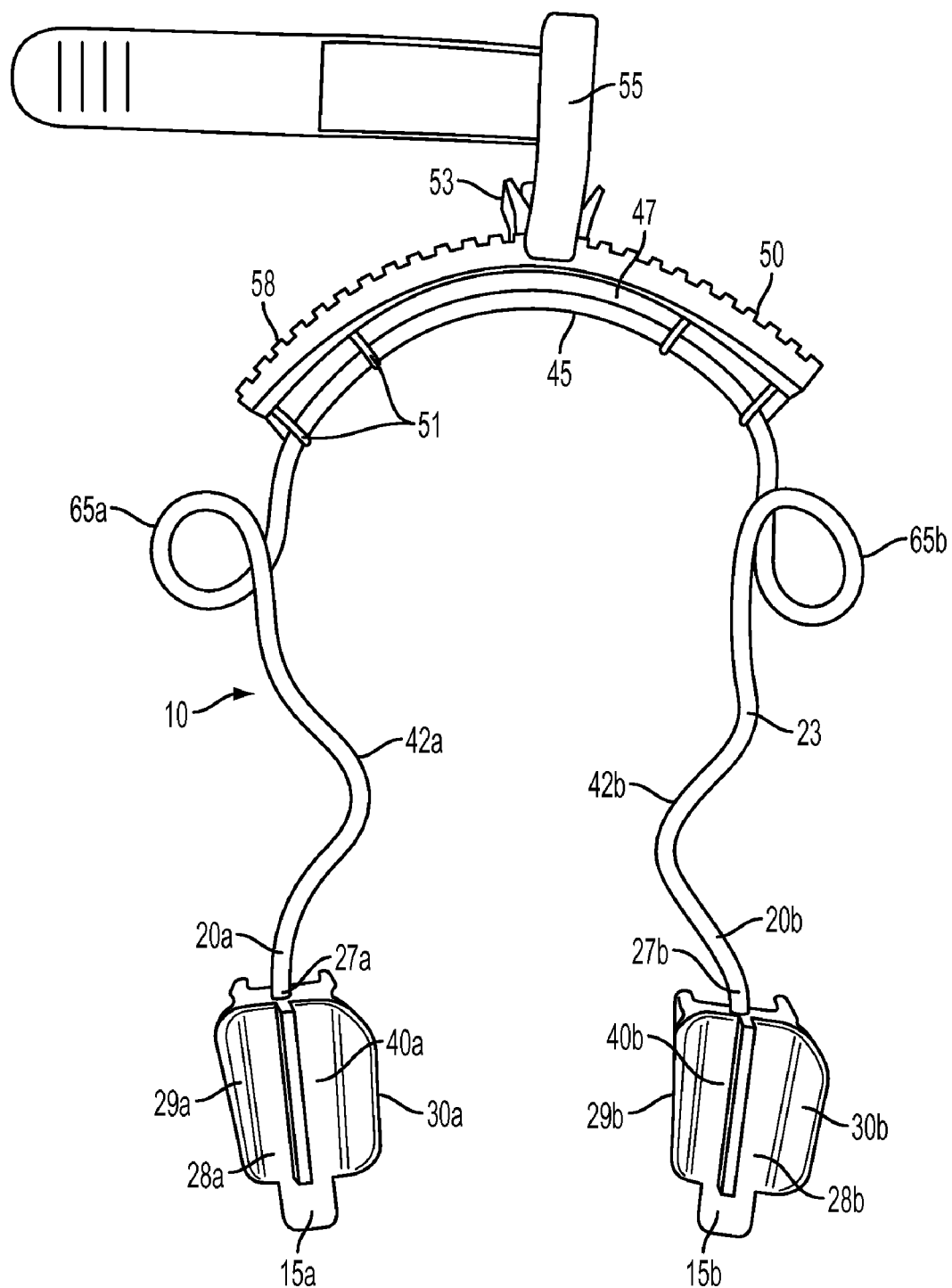
FIG. 1 is a photograph of the top plan view of the medical tube securing device.
Figure 2:
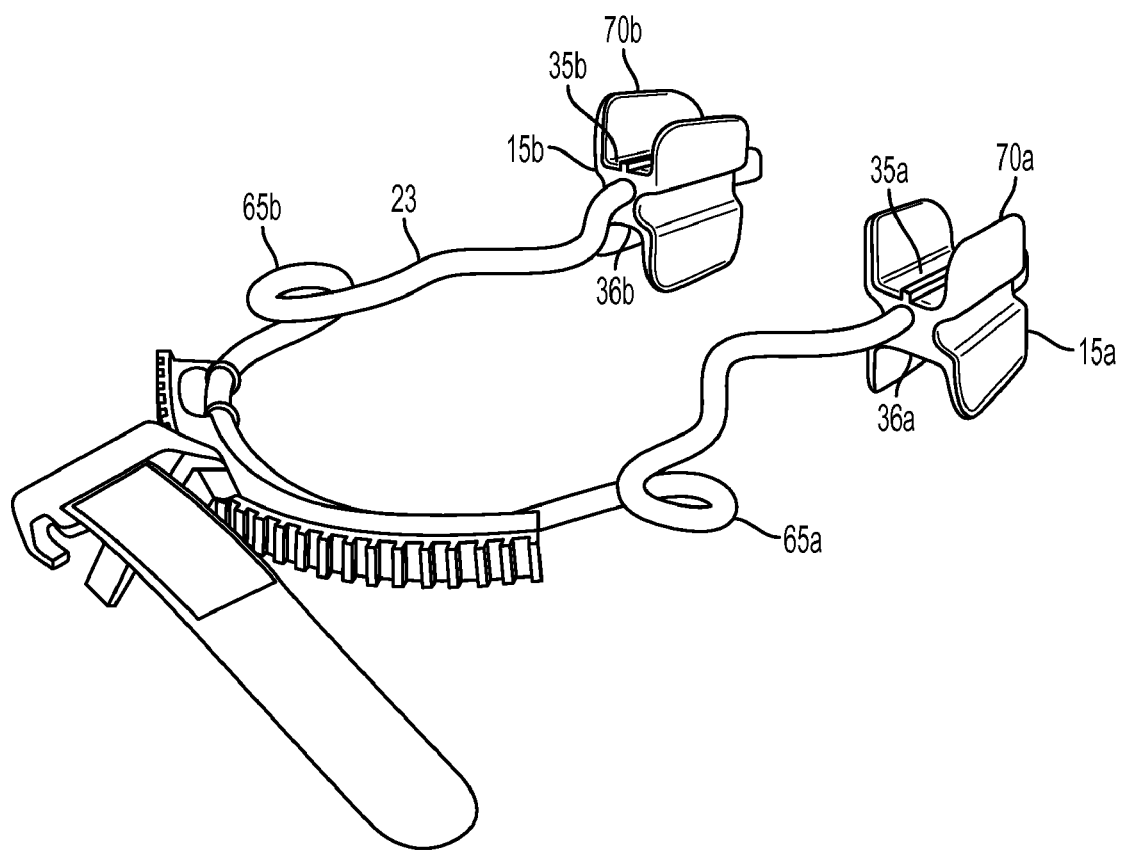
FIG. 2 is photograph of an orthogonal, left-front view of the medical tube securing device.

FIGS. 1-5 illustrate various views of the medical tube securing device 10. More specifically we see from FIG. 1 that the medical tube securing device 10 comprises a pair of left and right bite blocks 15a and 15b sized for receiving the upper and lower molars (the 2 or 3 upper and 2 or three lower teeth on each side of the mouth—not shown). The bite blocks 15a and 15b may be constructed of rubber or semi-rigid polymer block having a shore-A durometer hardness greater than about 50. In alternate embodiments of the invention the bite blocks 15a and 15b may comprise of a bio-compatible olefin polymer, a polyolefin homopolymer, a copolymer of olefins with vinyl esters, a copolymer of olefins with vinyl alcohol, mixtures of a polyolefin homopolymer, a copolymer of olefins with vinyl esters, a copolymer of olefins with vinyl alcohol, polyethylene, polypropylene, an ethylene-vinyl alcohol copolymer, an ethylene-vinyl acetate copolymer, an ethylene-propylene copolymer, a terpolymer of ethylene, a propylene ester, a vinyl ester, and blends and mixtures of the foregoing, zotefoam, rubber, and styrofoam. as well as other acceptable substitutes known in the art that are non-toxic, resilient and durable.

The bite blocks 15a and 15b are integrally connected with the distal end or terminus of the leg portions 20a and 20b of the u-shaped support frame 23 having symmetric halves. The terms "front," "near" or "proximal" and "rear," "removed" or "distal" being determined with respect to the position of the support frame 23.

Each bite block 15a and 15b has a front end 27a and 27b and a rear end 28a and 28b as well as left lateral sides 29a and 29b and right lateral sides 30a and 30b connecting the front and rear ends (27 and 28). From FIG. 2 we see that each bite block 15a and 15b also has a top surface 35a and 35b and a bottom surface 36a and 36b.

Returning once again to FIG. 1 we see that In the preferred embodiment, the top and bottom surfaces (35 and 36) of each bite block 15a and 15b are grooved or striated with ridges 40a and 40b in a manner perpendicular to the principal axis of the bit block 15a and 15b. The purpose of the ridges 40a and 40b is to provide a greater frictional contact point with the patient's molars so as to arrest movement of the medical tube securing device 10 during administration of care. However, alternate embodiments of said surfaces (35 and 36) are also contemplated by the inventors, including frictional surfaces of varying design known in the art and generally smooth, planar surfaces.

In the preferred embodiment, the support frame 23 is comprised of a malleable, rigid aluminum wire sheathed in polyvinyl chloride. A representative example of material appropriate for fabricating the support frame 23 is the intubating stylet sold under the trade name SATIN-SLIP™ by Tyco Healthcare Group LP (Nellcor Puritan Bennett Division, Pleasanton, Calif. 94588). In an alternate embodiment an injection-molded plastic/polymer may be used to construct the support frame with no loss of functionality. Each support frame 23 half begins at a respective bite block (15a and 15b) and then curves inwardly forming a concave indentation 42a and 42b so that contact with the corners of the mouth (not shown) is avoided. The support frame 23 halves then curve outwardly and extend forward beyond the lips (not shown). Forward of the lips, the frame halves curve inwardly and meet, forming a generally semicircular portion 45 that protrudes from the mouth. Along the front 47 of the semi-circular portion 45, a track 50 is either fixably or removably attached by attachment means 51. The track 50 is designed to engage with the tube holder 53 and clamping means 55 as is disclosed in the U.S. Pat. No. 5,490,504 to Vrona et al which is hereby incorporated by reference. The clamping means 55 may hold endotracheal and gastric tubes (also not shown).

Positioning means are provided for connecting the tube holder 53 to the track 50 which allows for the selective lateral positioning of the tube holder 53 and the tube (not shown) along the track 50. Such positioning means preferably takes the form of track means disposed on the outer surface 58 of the track 50 and shuttle means disposed on the tube holder 53 for engaging the track means and allowing lateral sliding of the shuttle and tube holder along the track means. On either side of the track 50 are means for connecting 65a and 65b a securing strap (not shown) that is placed around the lower rear of the head (not shown). In the preferred embodiment, the means for connecting 65a and 65b may comprise a continuous loop formed from each half of the support frame 23.

Turn our attention back again to FIG. 2. we can readily see that the preferred embodiment of the invention has bite blocks 15a and 15b with flanges 70a and 70b that are integral with both top and bottom surfaces (35 and 36) of each bite block 15a and 15b. The flanges help provide additional securing means by which to maintain the bite block 15a and 15b positioning by securing against the teeth of the patient (neither shown).

Figure 3:
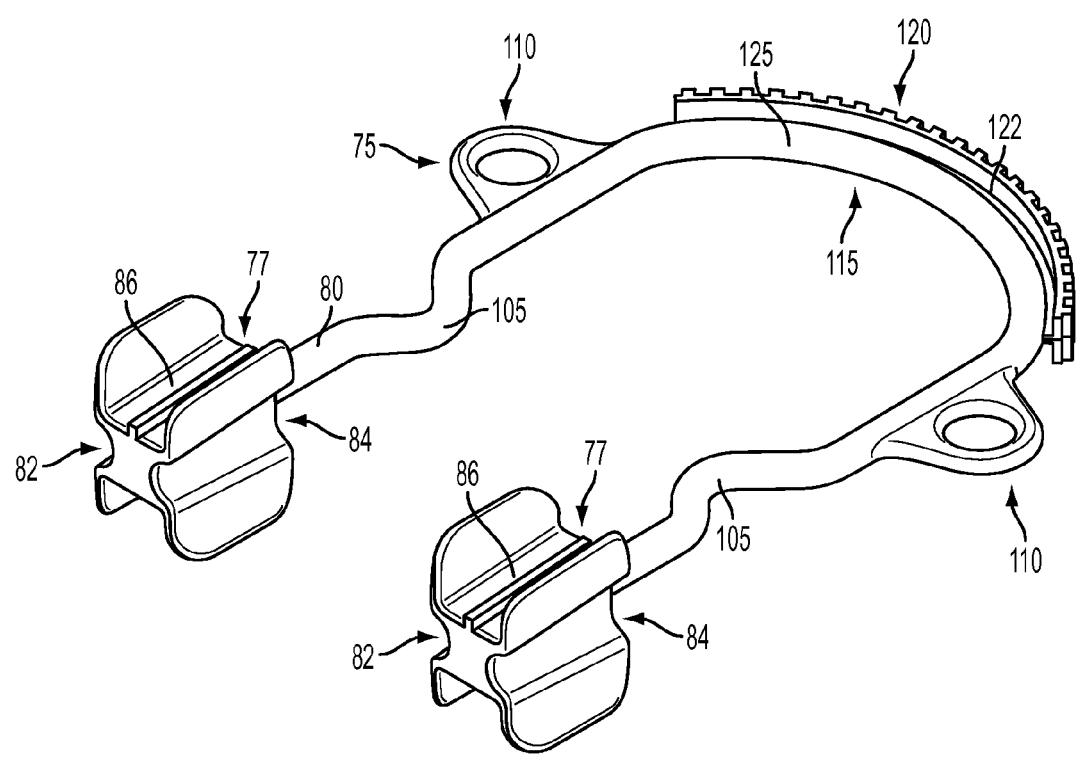
FIG. 3 is a drawing of the orthogonal, bottom-right view of the medical tube securing device.

An alternate embodiment of the invention shown in FIG. 3. Here the bite block is generally denoted by the reference number 75. The bit block 75 comprises a specialized bite block portion 77 with a fixedly attached support frame 80. Generally, the bite block portion 77 is preferably formed of molded, medical grade plastic or other similarly hard material. Specifically, the bite block portion 77 may be constructed of rubber or semi-rigid polymer block having a shore-A durometer hardness greater than about 50. In alternate embodiments of the invention the bite block portion 77 may comprise of a bio-compatible olefin polymer, a polyolefin homopolymer, a copolymer of olefins with vinyl esters, a copolymer of olefins with vinyl alcohol, mixtures of a polyolefin homopolymer, a copolymer of olefins with vinyl esters, a copolymer of olefins with vinyl alcohol, polyethylene, polypropylene, an ethylene-vinyl alcohol copolymer, an ethylene-vinyl acetate copolymer, an ethylene-propylene copolymer, a terpolymer of ethylene, a propylene ester, a vinyl ester, and blends and mixtures of the foregoing, zote-foam, rubber, and styrofoam. as well as other acceptable substitutes known in the art that are non-toxic, resilient and durable. In general, the bite block is designed to be placed between the teeth on both sides of the mouth thereby to hold the teeth apart.

The bite block portion 77 is preferably wedge-shaped and defines a posterior portion 82 and an anterior portion 84. The bite block portion 77 further includes an upper teeth engagement surface 86 and a lower teeth engagement surface 87 (see FIG. 4). While the teeth engagement surfaces (86 and 87) preferably engage the molar teeth of the patient, it is understand that these surfaces can also engage with the canine or bicuspid teeth. The wedge-shaped bite block portion 77 is angled such that the teeth engagement surfaces 86 and 87 gradually become farther apart in the direction from the posterior portion 82 toward the anterior portion 84 as best seen in FIG. 5. The angle of the wedge-shaped bite block portion 77 is made according to the size of the accompanying substituted airway product. In this way, the practitioner is assured that the patient is prevented from biting down on and thereby occluding or severing the breathing or exiting tube (not shown). The teeth engagement surfaces (86 and 87) may also be formed so as to be serrated or otherwise characterized to be optimally form-fitting with engaging teeth (not shown), to include irregular patterns, channels (FIG. 4 reference numeral 90) and the like. Further, the teeth engagement surfaces (86 and 87) may take the form of a pliable surface such that the teeth can grip the bite block portion 77.

Figure 4:
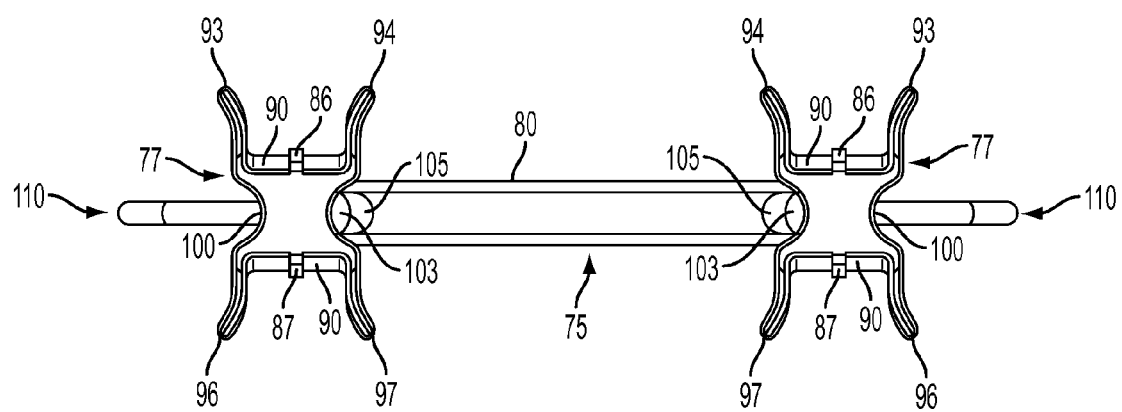
FIG. 4 is a drawing of the rear elevation view of the medical tube securing device.
Figure 5:
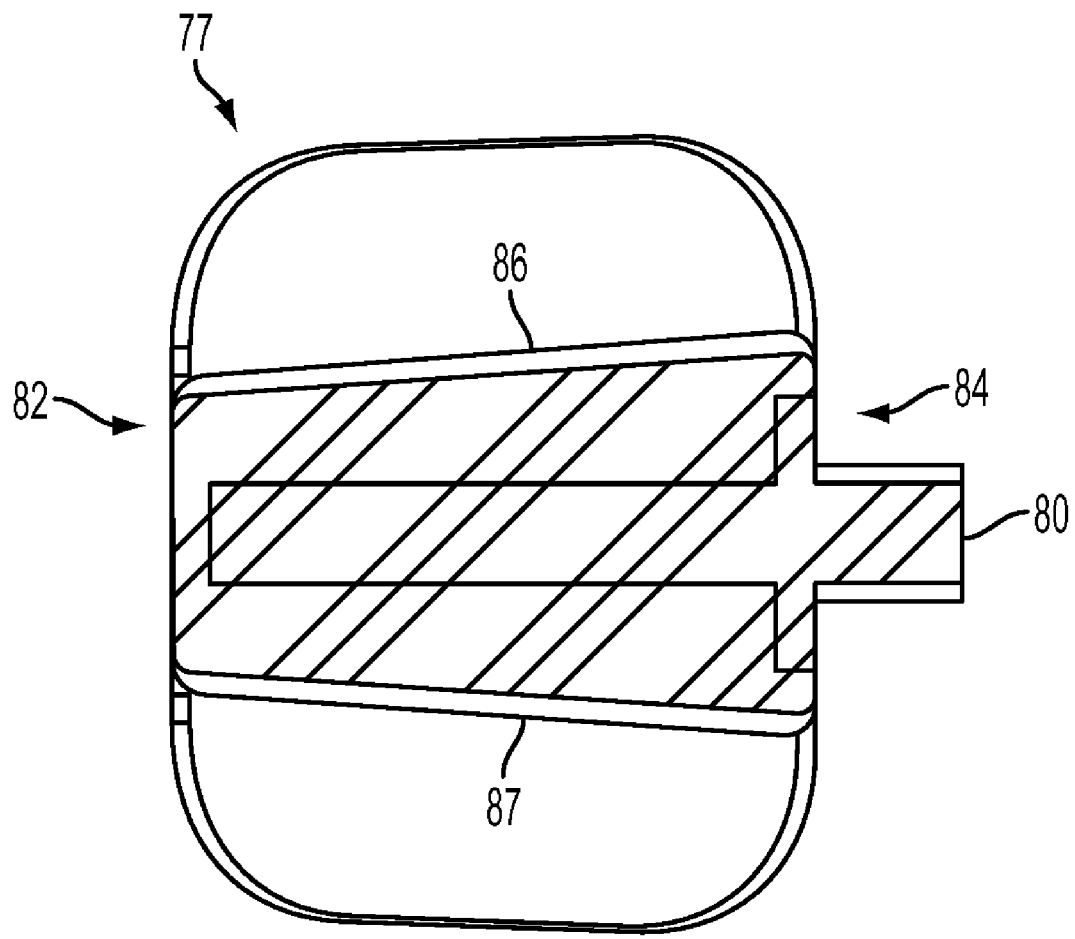
FIG. 5 is a drawing of the side elevation, cross-section view of the medical tube securing device bite block portion.

In FIG. 4 we see a pair of upper flanges (93 and 94) extend from the upper side of the bite block portion 77, on the medial and lateral borders thereof, respectively. A pair of lower flanges (96 and 97) likewise extends from a lower side of the bite block portion 77 on the medial and lateral borders respectively. The four flanges (93, 94, 96 and 97) function together to retain the bite block 75 in place within the patient's mouth. It is important to understand that the designations "upper" and "lower" when describing referenced elements 86, 87, 93, 94, 96 and 97 are simply for understanding the drawings as the bite block 75 may be rotated 180 degrees. The upper and lower lateral flanges (93 and 96) are dimensioned to be positioned between the patient's teeth and cheek and are designed to prevent the lateral movement of the bite block 75 towards the patient's tongue (not shown). The upper and lower medial flanges (94 and 97) are dimensioned to be positioned between the patient's tongue and teeth and are designed to prevent the lateral movement of the bit block 75 towards either of the patent's cheeks (not shown). The four flanges (93, 94, 96 and 97) are angled away from the bite block portion 77 in order to prevent the flanges from irritating the gums and alveolar ridges. The four flanges (93, 94, 96 and 97) also serve to protect the patient from biting his tongue or the mucosa of the cheeks. Molded grooves (100 and 103) are positioned midway between the upper and lower flanges and function to permit airway device catheters (not shown) to pass into the patient's posterior oropharynx (not shown).

Turning now, back to FIG. 3, we see that the support frame 80 itself comprises two concave indentations 105; two apertures 110 radiating laterally to and integral with the support frame 80; and, a semicircular portion 115 itself comprising a track 120. The support frame 80 is preferably constructed from injection-molded plastic/polymer or any material suitable for long-term use in a patient's oral cavity and known in the art. The two concave indentations 105 are designed to navigate around the corners of the patient's mouth (not shown) so as to avoid contact when properly positioned within the oral cavity. The two apertures 110 are designed to allow the fixation of one end of a securing strap (not shown) to one aperture 110, so that the free end of the strap (not shown) can be lead around the head of the patient (not shown)

to the other aperture 110 where the free-end of the strap (not shown) is, again, affixed. It is understood that the strap may be positioned around other parts of the patient's body such as the neck, or to structures separate from the body (not shown). Forward of the lips, the support frame 80 forms a generally semicircular portion 115 that protrudes beyond the mouth of the patient (not shown). Along the front 122 of the semicircular portion 115 a track 120 is integrally formed as part of the molded support frame 80. In the preferred embodiment, the track 120 is designed to engage with a tube holder and clamping means for holding endotracheal and gastric tubes as is disclosed in the U.S. Pat. No. 5,490,504 to Vrona et al which is hereby incorporated by reference. However, it is understood that the track 120 may allow for the selective lateral positioning of any clamping device that is capable of being mounted on the track 120. Further, it is understood that the bite block 75 is also capable of functioning with any clamping device capable of mounting on the front 122 or rear 125 of the semicircular portion 115 of the support frame 80.

While a specific embodiment of the invention will be shown and described in detail to illustrate the application of the principles of the invention, it will be understood that the invention may be embodied otherwise without departing from such principles.

What is claimed is:

1. A medical tube securing device for a patient comprising: at least one bite block having a front end and a rear end as well as left lateral sides and right lateral sides connecting the front and rear ends, and a top and bottom surface, said top and bottom surfaces being constructed so as to present a frictional plane, said left and right lateral sides extending in generally upwards and downwards directions to form flanges; a generally arcuate support frame integral with said bite block, said frame being characterized by at least one inwardly recessed portion and at least one integral aperture abutting the recessed portion operable to receive a securing strap for securing the medical tube securing device to the patient; a means for adjustably mounting a medical tube over the mouth of the patient comprising at least one track; wherein the track is capable of receiving a tube holder that is slidably connected to said track and having an arm extending in a direction perpendicular to said track; a shuttle attaching said tube holder to said track and allowing lateral sliding of said tube holder along the length of said track; and an elongated, flexible strap with one end attached to said arm of said tube holder and a free length extending in a direction transverse to said arm, a clamping member hingedly attached to said tube holder, and releasable latching means for locking said clamping member along said arm to secure said strap around a tube when a segment of said strap is inserted between said clamping member and said arm.

2. The device of claim 1, wherein the frictional plane is grooved or striated with ridges in a manner perpendicular to the principal axis of the bite block.

3. The device of claim 1, wherein the bite block is constructed of rubber.

4. The device of claim 1, wherein the bite block is constructed of a semi-rigid polymer block having a shore-A durometer hardness greater than 50.

5. The device of claim 1, wherein the bite block is constructed of a material selected from the group consisting of: a bio-compatible olefin polymer, a polyolefin homopolymer, a copolymer of olefins with vinyl esters, a copolymer of olefins with vinyl alcohol, mixtures of a polyolefin homopolymer, a copolymer of olefins with vinyl esters, a copolymer of olefins with vinyl alcohol, polyethylene, polypropylene, an ethylene-vinyl alcohol copolymer, an ethylene-vinyl acetate copolymer, an ethylene-propylene copolymer, a terpolymer of ethylene, a propylene ester, a vinyl ester, zotefoam, tyrofoam, and blends and mixtures of the foregoing.

6. The device of claim 1, wherein the support frame is constructed of a material selected from the group consisting of a wire sheathed in polyvinyl chloride and injection-molded polymers.

\* \* \* \* \*